(12) United States Patent
Wollnik

(10) Patent No.: US 7,772,548 B2
(45) Date of Patent: Aug. 10, 2010

(54) "DROPLET PICKUP ION SOURCE" COUPLED TO MOBILITY ANALYZER APPARATUS AND METHOD

(75) Inventor: Hermann Wollnik, Fernwald (DE)

(73) Assignee: Shimadzu Corporation, Kyoto-fu (JP)

( * ) Notice: Subject to any disclaimer, the term of this patent is extended or adjusted under 35 U.S.C. 154(b) by 338 days.

(21) Appl. No.: 12/118,763

(22) Filed: May 12, 2008

(65) Prior Publication Data

US 2009/0278036 A1    Nov. 12, 2009

(51) Int. Cl.
*B01D 59/44* (2006.01)
(52) U.S. Cl. ....................................... 250/288
(58) Field of Classification Search ................. 250/288
See application file for complete search history.

(56) References Cited

U.S. PATENT DOCUMENTS

| | | | |
|---|---|---|---|
| 7,057,166 | B2 | 6/2006 | Guevremont et al. |
| 7,193,223 | B2 * | 3/2007 | Franzen ..................... 250/425 |
| 7,335,897 | B2 | 2/2008 | Takáts et al. |
| 2007/0029477 | A1 | 2/2007 | Miller et al. |
| 2007/0176113 | A1 | 8/2007 | Shiea et al. |

OTHER PUBLICATIONS

Shiea et al. "Electrospray-assisted laser desorption/ionization mass spectrometry for direct ambient analysis of solids" Rapid Commun. Mass Spectrom. 2005; 19: pp. 3701-3704.

Chang et al. "Detecting Large Biomolecules from High-Salt Solutions by Fused-Droplet Electrospray Ionization Mass Spectrometry" Analytical Chemistry, vol. 74, No. 11 Jun. 1, 2002, pp. 2465-2469.
Takáts et al. "Mass Spectrometry Sampling Under Ambient Conditions with Desorption Electrospray Ionization" www.sciencemag.org SCIENCE vol. 306, Oct. 15, 2004.
Eiceman "Ion-mobility spectrometry as a fast monitor of chemical composition" trends in analytical chemistry, vol. 21, No. 4, 2002, pp. 259-275.
Myung, S., Wiseman, J.M., Valentine, S.J., Takáts, Z., Cooks, R.G., Clemmer, D.E., "Coupling desorption electrospray ionization with ion mobility/mass spectrometry for analysis structure: evidence for desorption of folded and denatured states," 2006, Journal of Phys. Chem. vol. 110, p. 5045-5051, Feb. 14, 2006, [online]. Retrieved on [Jun. 16, 2009]. Retrieved from: <URL: http://pubs.acs.org/doi/pdf/10.10211/jp052663e>.

(Continued)

*Primary Examiner*—Kiet T Nguyen
(74) *Attorney, Agent, or Firm*—Sughrue Mion, PLLC

(57) ABSTRACT

An ion mobility analyzer includes at least one of a "differential mobility analyzer", an "ion mobility spectrometer" and a "differential mobility spectrometer", to which charged molecules of interest are fed. Ions are fed to the ion mobility analyzer from a "droplet pickup ion source" including an electrospray ion source at a capillary end, from which charged droplets formed from a solvent mixture having substantially none of the molecules of interest emerge. The charged droplets are pulled by an electric field into a "pickup region" filled with a buffer gas at a pressure or a region close to the surface of a sample, where the charged droplets incorporate the molecules of interest and transfer the charge of the charged droplets to the molecules of interest, when the liquid in the charged droplets has evaporated in a heated desolvation region that is separate or integral with respect to the "pickup region".

21 Claims, 4 Drawing Sheets

OTHER PUBLICATIONS

Kaur-Atwal, G., Weston, D.J., Green, P.S., Crosland, S., Bonner, P.L.R., Creaser, C.S., "Analysis of tryptic peptides using desorption electrospray ionization combined with ion mobility spectrometry/mass spectrometry," 2007, Rapid Communications in Mass Spectrometry, Vo. 21, p. 1131-1138, Jan. 2007. [online]. Retrieved from the Internet on [Jun. 16, 2009]. Retrieved from: <URL: httpf/www3.interscience.wiley.com/cgi-bin/fulltext/114128667/PDFSTART>.

Koeniger, S.L., Merenbloom, 5.1., Valentine, S.J., Jarrold, M.F., Udseth, H.R., Smith, R.D., Clemmer, D.E., "An IMS-IMS analogue of MS-MS," 2006, Analytical Chemistry Vo., 78, No. 12, p. 4161-4174, Jun. 15, 2006. [online]. Retrieved from the Internet on [Jun. 16, 2009]. Retrieved from: <URL: http://www.indiana.edu/~clemmer/Publications/pub%20112.pdf>.

Venter, A., Sojka, P.E., Cooks, R.G., "Droplet dynamics and ionization mechanisms in desorption electrospray ionization mass spectrometry,"2006, Analytical Chemistry vol. 78, No. 24, p. 8549-8555, Dec. 15, 2005 [online]. Retrieved from the Internet on [Jun. 16, 2009]. Retrieved from : <URL: http://www.umiacs.umd.edu/~nedwards/teaching/BCHM676_Spring_2007/papers/analchem.20.06.78.8549.pdf>.

* cited by examiner

"DROPLET PICKUP ION SOURCE" COUPLED TO MOBILITY ANALYZER APPARATUS AND METHOD

BACKGROUND OF THE INVENTION

1. Technical Field

The present invention relates to ion sources for molecular ions and to gas-filled ion mobility analyzers, and a related apparatus and method therefore.

2. Related Art

Related art ion sources must produce ions gently in order to not fragment the molecules of interest. This may be done via electrospray ion sources, in which a conductive liquid is pushed through a small capillary. At the capillary exit, small droplets are formed, of which a large number is charged and accelerated to form a diverging beam. If some of these charged droplets contain a molecule of interest and the liquid of the droplet evaporates, the droplet charge can remain on the molecules. Such ion sources include:

1. Related art "electrospray ion sources" in which molecules of interest are dissolved in the conductive liquid with which the ion source is fed. This requires that (a) the molecules of interest are capable of being dissolved in the liquid, (e.g., a mixture of different solvents), and (b) the electrospray ion source is capable of efficiently producing charged droplets from the liquid.

2. "Droplet pickup ion sources" that allow sample treatment to be used for many applications. Such "droplet pickup ion sources" include an electrospray ion source that forms charged droplets from a mixture of solvents in which no appreciable quantity of the molecules of interest is dissolved while the molecules of interest are incorporated into the droplets when they pass through a "pickup region" in which the molecules of interest exist. In this "pickup region", the charged droplets can incorporate these molecules if (a) the molecules of interest exist in this "pickup region" as free molecules that can adsorb at the surfaces of the charged droplets that had been brought into this region (such free molecules can for instance be desorbed by a laser beam from a solid or liquid sample), if (b) the molecules of interest exist on the surface of a solid or liquid sample within the "pickup region" from where they can adsorb at the surfaces of the charged droplets directly when these interact with this surface and if (c) the molecules of interest have been dissolved in independently formed neutral droplets that can fuse with the charged droplets in the "pickup region".

A related art version of the "droplet pickup ion sources" has been used, but only as ion sources for mass spectrometers.

In the related art mobility analyzers, electric fields drag clouds of molecular ions through a gas with an average drag velocity that increases with the magnitude of the electric field. The proportionality constant is the ion mobility that increases substantially with the inverse of the molecule cross section. Such mobility analyzers include:

1. "Differential Mobility Analyzers (DMA)" in which a substantially constant electric field drags ions substantially perpendicular to a gas stream. Depending on the time the ions of interest need to cross the gas stream, the gas flow moves the ions a shorter or a longer distance in a direction perpendicular to the electric field.

2. "Ion Mobility Spectrometers (IMS)" in which a substantially constant electric field drags ions through a stationary gas or through a gas that moves substantially parallel to the electric field. Depending on the average drag velocity of the ions of interest, these ions pass in different times through the region in which the electric field exists. This electric field is static, but can be pulsed in parts, or take the form of a traveling wave.

3. "Differential Mobility Spectrometers (DMS)", wherein in a given gas, the mobilities of different ions vary with the magnitude of the electric field in different ways. In such a DMS, an electric RF-field drags ions back and forth substantially perpendicular to a gas stream between two electrodes. The waveform of the RF-field is chosen to be asymmetric. As a result, for a short time a high field drags the ions in a first direction and for a longer time a low field drags the ions in a second and opposite direction. Thus, the ions that can pass between the two electrodes are ions having a specific ratio between their high-field mobility and their low-field mobility, depending on the asymmetry of the RF-waveform. Such systems have been developed with electric fields formed between planar electrodes or between electrodes that form concentric cylinders.

SUMMARY OF THE INVENTION

According to aspects of the present invention, "droplet pickup ion sources", which have only been used in the related art to introduce ions into mass spectrometers, are modified such that the produced molecular ions are entered into gas filled mobility analyzers. In this case one can:

1. use at least one (e.g., lightweight and inexpensive) mobility analyzer to record the mobility spectra of the ions, as compared with related art bulky and costly mass spectrometers.

2. use at least one (e.g., lightweight and inexpensive) mobility analyzer as a mobility filter, from which only ions of a range of mobilities enter into a mass spectrometer, or ions whose mobilities "K" are smaller than a maximum "$K_{max} \geq K$" or larger than a minimum "$K_{min} < K$". In this case, one obtains mass spectra of mobility selected ions that provide a substantially higher molecule specificity than mass spectra of ions of all mobilities. From this information, one can also construct a two-dimensional intensity distribution of ion masses and ion mobilities.

In the "droplet pickup ion source", molecules of interest exist in or enter into a "pickup region" where they can be incorporated into charged droplets entered into the same "pickup region" from an electrospray ion source. The charged droplets are formed by the electrospray ion source from a mixture of solvents in which no more than negligible amounts of the molecules of interest had been dissolved. When the liquid of the charged droplets evaporates, the droplet charge is transferred to the incorporated molecules of interest.

The molecules of interest may be brought into the "pickup region" as free molecules that can adsorb at the surfaces of the charged droplets when the molecules of interest have been brought into the "pickup region" as a vapor within a buffer gas or when the molecules of interest have been desorbed from the surfaces of solid or liquid samples by the impact of a laser beam (see FIG. 1) or of a beam of energetic particles. The molecules of interest can also exist in the "pickup region" on the surface of a solid or liquid sample with which charged droplets interact directly in which case the molecules of interest can also be incorporated to the charged droplets (see FIG. 2). When many mobility spectra can be recorded or many mass spectra of mobility selected ions, the vapor within a buffer gas is replaced by the effluent of a gas chromatograph or when the static liquid sample is replaced by the effluent of a liquid chromatograph in both cases the appearance of new molecules in the effluent of the chromatographs can be recorded or monitored. Also the local distribution of molecules of interest on the surface of the sample can be recorded when the laser beam is rastered across the surface of a liquid or a solid sample, or when the position of interaction of the plume of charged droplets with the surface of the sample is rastered across the solid or liquid sample.

Also, the molecules of interest may be brought into the "pickup region" as free molecules that can adsorb at the surfaces of the charged droplets when the molecules of interest have been brought into the "pickup region" either directly (see FIG. 3) and/or through some "mixing chamber" (see FIG. 4) within a buffer gas as vapors. This may be of interest when many mobility spectra are recorded or many mass spectra of mobility selected ions, for instance to record or to monitor the appearance of new molecules in the effluent of a gas chromatograph (see FIG. 3).

The molecules of interest may also be brought into the "pickup region" when the molecules of interest were incorporated in independently formed "neutral droplets" floating in a buffer gas and brought into the "pickup region" either directly (see FIG. 3) and/or through some "mixing chamber" (see FIG. 4). The transfer of thermolecules of interest to the charged droplets can then be achieved when the neutral droplets fuse with charged droplets in the "pickup region" (see FIG. 3) and/or are partially already in the mixing chamber (see FIG. 4), or alternatively, when the liquid in the neutral droplets evaporates and the molecules of interest become free molecules that can adsorb at the surfaces of charged droplets in the "pickup region" (see FIG. 3) and/or partially already in the mixing chamber (see FIG. 4).

The incorporation of molecules of interest into the neutral droplets can be achieved by having the molecules of interest dissolved in the liquid the neutral droplets are formed of, which can be the liquid in a syringe or the liquid in the capillary of a liquid chromatograph, or by having these molecules adsorb at the neutral droplets in some containment upstream, where they can exist as free molecules (e.g., desorbed from a sample by a laser beam or a beam of energetic particles or as vapors in some buffer gas, for instance the effluent of a gas chromatography.

In the foregoing cases, the appearance times of different molecules in a chromatogram can be monitored by changes in mobility spectra or with increased molecule specificity by changes in mass spectra of mobility selected molecules. This can be considered in comparison with the related art rough monitoring by varied light absorption in the effluent of the chromatograph, or the change of mass spectra obtained from ions of all available mobilities.

BRIEF DESCRIPTION OF THE DRAWINGS

The above and/or other aspects of the presents invention will become apparent and more readily appreciated from the following description of the exemplary embodiments, taken in conjunction with the accompanying drawings, in which.

DETAILED DESCRIPTION OF THE INVENTION

Figure 1:
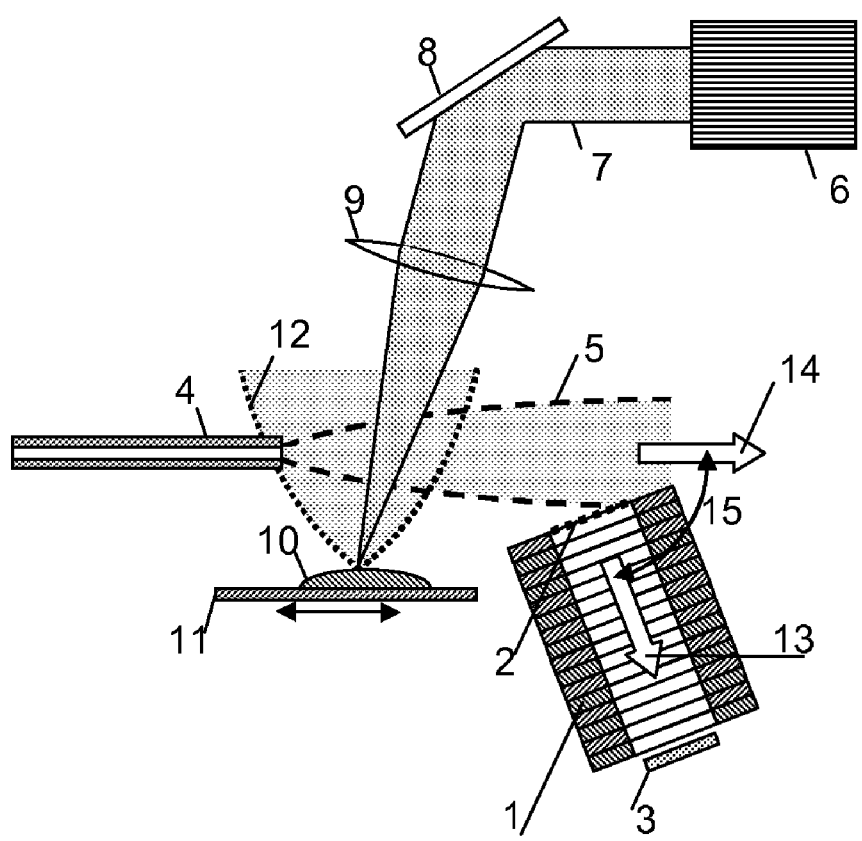
FIG. 1 is a schematic view of a first exemplary, non-limiting embodiment of a "droplet pickup ion source" and a mobility analyzer.

Exemplary embodiments of the present invention will be described in greater detail with reference to the accompanying drawings. In the following description, the same drawing reference numerals are used for the same elements in both drawings. The matters defined in the description such as a detailed construction and arrangement of elements are nothing but the ones provided to assist in a comprehensive understanding of the invention. Thus, it is apparent that the present invention can be carried out without being limited to those defined matters. Also, well-known functions or constructions are not described in detail since they would obscure the invention in unnecessary detail.

FIG. 1 is a schematic view of a first exemplary, non-limiting embodiment of a "droplet pickup ion source" and a mobility analyzer. A mobility analyzer 1 is provided, into which ions are transferred through an entrance grid or aperture 2, and in which mobility analyzed ions can be recorded in an ion detector 3, or entered into a mass spectrometer. The capillary 4 of an electrospray ion source as well as a boundary of a beam 5 of accelerated charged droplets is also shown. A laser 6 generates a beam 7 that is directed by a tiltable mirror 8 and is passed through a lens 9 to a solid or liquid sample 10 that optionally rests on a movable support 11.

The laser beam 7 can desorb molecules of interest from the sample 10, in which case the molecules leave the sample 10 in a plume 12. The direction 13 of the ion motion in the mobility analyzer 1 is inclined relative to the main direction 14 of the beam of charged droplets, by an angle of inclination 15.

The ion mobility analyzer 1 is depicted as an ion mobility spectrometer (IMS). Into the mobility analyzer 1, ions are accelerated through the grid 2; in the mobility analyzer 1, the ions are pulled by another electric field through a buffer gas and recorded in the ion detector 3.

From the appearance times of these ion signals, one can deduce the ion velocities in the mobility analyzer and thus the corresponding ion nobilities. As an alternative, one can also replace this detector 3 with an ion shutter that opens for a period, during which ions of a specific mobility may pass toward the entrance of a sequentially arranged mass spectrometer.

From the end of the electrospray capillary 4, charged droplets can be accelerated into the beam 5. In the shown "droplet pickup ion source", the charged droplets are assumed to be formed from a conductive mixture of solvents, in which substantially no appreciable amounts of the molecules of interest were dissolved. These molecules of interest may instead be adsorbed at the surfaces of the charged droplets in the "pickup region" as free molecules after they have been desorbed from some sample by the laser beam 7. This laser beam is arranged at an angle, and deflected by the mirror 8 and focused by the lens 9 into a fine spot on the sample 10, optionally positioned by the movable support 11.

The sample 10 may be:

1. a solid sample, in which case one can investigate molecules at selected spots on the surface of the sample; accordingly, the spot location is changed from one laser pulse to the next by the mirror 8 and/or the movable support 11;

2. a solid sample over which the laser beam is scanned (e.g., as on a television screen), so that the obtained mobility spectra or mass spectra of mobility selected molecules reveal the local distribution of different molecules;

3. a liquid sample, in which case the laser spot can remain fixed while the liquid renews its surface by convection; and/or 4. a liquid sample that is the effluent of a liquid chromatograph, so that the mobility spectra change with time when new molecules of interest appear in the chromatogram.

In the foregoing cases, the incorporated molecules of interest are ionized when the liquid of the droplets evaporates and the droplet charge is transferred to the incorporated molecules.

In the "droplet pickup ion-source" the capillary 4 is the capillary of an "electrospray ion source". Further, the main part of the "pickup region" is the overlap of the beam 5 of charged droplets and the plume 12 of desorbed free molecules. The direction of ion motion 13 in the mobility analyzer is inclined to the direction 14 of the beam of charged droplets at the inclination angle 15, which is chosen such that most of the molecule ions but only a few of the charged droplets, can enter the ion mobility spectrometer.

Figure 2:
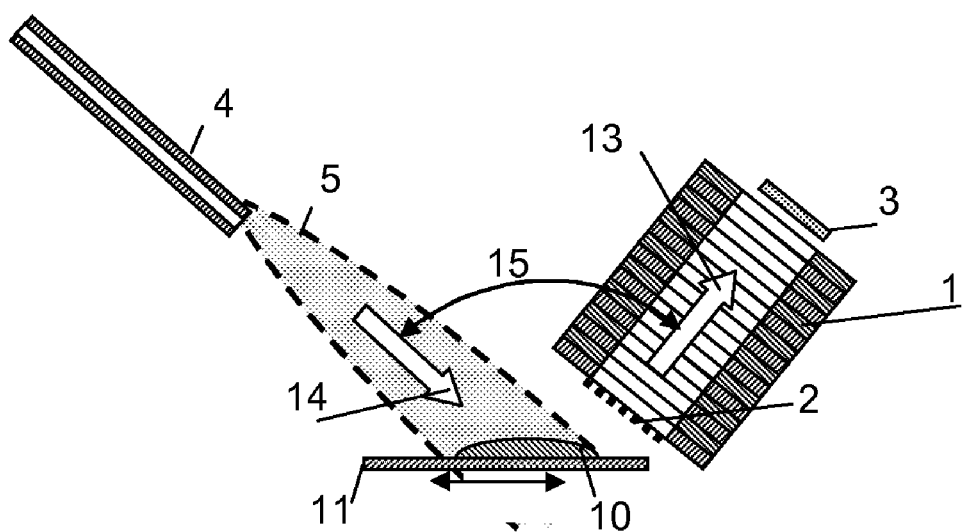
FIG. 2 is a schematic view of a second exemplary, non-limiting embodiment of a "droplet pickup ion source" and a mobility analyzer.

FIG. 2 is a schematic view of a second exemplary, non-limiting embodiment of a "droplet pickup ion source" and a mobility analyzer. A mobility analyzer 1 is provided, into which ions are transferred through an entrance grid or aperture 2, and in which mobility analyzed ions can be recorded in an ion detector 3, or entered into a mass spectrometer. The capillary 4 of an electrospray ion source as well as a boundary of a beam 5 of accelerated charged droplets is also shown. In this embodiment the beam of charged droplets is directed towards the sample 10 which can be one of a solid and a liquid. The sample rests on a movable support 11 so that one can vary the region where the charged droplets impact on the sample, e.g. the region where the charged droplets interact with the sample surface and pickup the molecules of interest.

The direction 13 of the ion motion in the mobility analyzer 1 is inclined relative to the main direction 14 of the beam of charged droplets, by an angle of inclination 15 and both are inclined relative to the surface of the simple.

Similar to the first embodiment the ion mobility analyzer 1 is depicted as an ion mobility spectrometer (IMS). Into the mobility analyzer 1, ions are accelerated through the grid 2; in the mobility analyzer 1, the ions are pulled by another electric field through a buffer gas and recorded in the ion detector 3. From the appearance times of these ion signals, one can deduce the ion velocities in the mobility analyzer and thus the corresponding ion mobilities. As an alternative, one can also replace this detector 3 with an ion shutter that opens for a period, during which ions of a specific mobility may pass toward the entrance of a sequentially arranged mass spectrometer.

Figure 3:
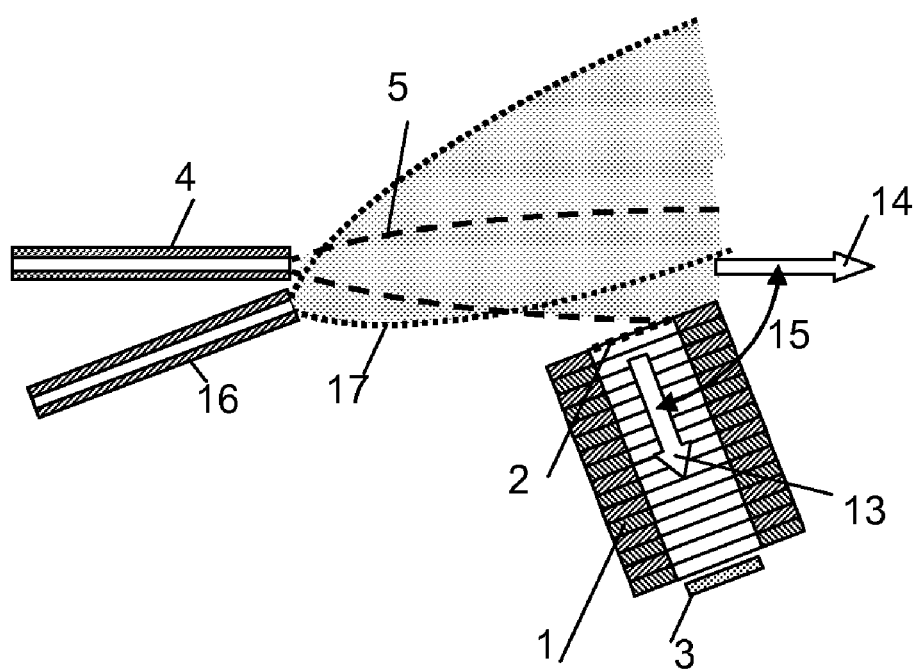
FIG. 3 is a schematic view of a third exemplary, non-limiting embodiment of a "droplet pickup ion source" and a mobility analyzer.

FIG. 3 is a schematic view of a second exemplary, non-limiting embodiment of a "droplet pickup ion source" and a mobility analyzer. A mobility analyzer 1 is provided, into which ions are transferred through an entrance grid or aperture 2, and in which mobility analyzed ions can be recorded in an ion detector 3, or entered into a mass spectrometer. The capillary 4 of an electrospray ion source as well as a boundary of a beam 5 of accelerated charged droplets is also shown.

A capillary 16 is also provided from which a buffer gas emerges as a plume 17 that emerges transporting vapors or neutral droplets formed in a separate generator to the "pickup region". The direction 13 of the ion motion in the mobility analyzer is inclined relative to the direction 14 of the beam of charged droplets by an inclination angle 15.

Similar to the first embodiment, the ion mobility analyzer 1 is depicted as an ion mobility spectrometer (IMS). Into the mobility analyzer 1, ions are accelerated through the grid 2; in the mobility analyzer 1, the ions are pulled by another electric field through a buffer gas and recorded in the ion detector 3. From the appearance times of these ion signals, one can deduce the ion velocities in the mobility analyzer and thus the corresponding ion mobilities. As an alternative, one can also replace this detector 3 with an ion shutter that opens for a period, during which ions of a specific mobility may pass toward the entrance of a sequentially arranged mass spectrometer.

From the capillary 4, charged droplets are accelerated to form a diverging beam 5. In the shown "droplet pickup ion source", the charged droplets may be formed from a conductive mixture of solvents in which substantially no appreciable amounts of the molecules of interest were dissolved. These molecules of interest may instead be incorporated into the charged droplets in a "pickup region". This can occur when in the "pickup region":

1. these charged droplets fuse with neutral droplets formed independently from a mixture of solutions in which the molecules of interest were dissolved or of a mixture of solutions that contained no appreciable amount of the molecules of interest in which case, however, these neutral droplets had picked up the molecules of interest when they interacted with the surface of a solid or liquid sample or when they passed through a gas-filled volume incorporating there the molecules of interest. These neutral droplets emerge from the second capillary 16 transported by a buffer gas that forms the plume 17; or 2. free molecules of interest exist in the plume 17 after the liquid of neutral droplets evaporated; or 3. vapors of the molecules of interest exist in the plume 17. If the effluent of a gas chromatograph is investigated, such vapors can change over time, which requires that a number of mobility spectra or a number of mass spectra of mobility selected molecules are recorded.

In the foregoing cases, the incorporated molecules of interest are ionized when the liquid of the charged droplets evaporates and the droplet charge is transferred to the incorporated molecules.

The main part of the "droplet pickup ion-source" is the "pickup region", e.g. the overlap of the beam 5 of charged droplets and the buffer gas plume 17 transporting vapors and/or neutral droplets. The direction of the motion 13 of ions in the mobility analyzer is inclined to the direction 14 of the beam of charged droplets by an inclination angle 15 that may be chosen such that most of the molecule ions but substantially none of the neutral and charged droplets enter the ion mobility spectrometer.

Figure 4:
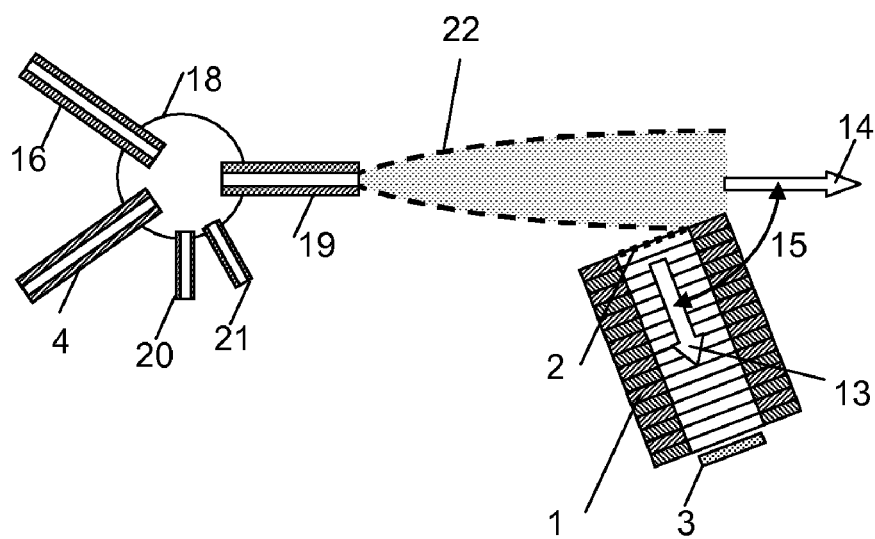
FIG. 4 is a schematic view of a fourth exemplary, non-limiting embodiment of a "droplet pickup ion source" and a mobility analyzer.

FIG. 4 is a schematic view of a third exemplary, non-limiting embodiment of a "droplet pickup ion source" and a mobility analyzer.

A mobility analyzer 1 is provided, into which ions are transferred through an entrance grid or aperture 2, and in which mobility analyzed ions can be recorded in an ion detector 3, or entered into a mass spectrometer. Also a "mixing chamber" 18 is provided, into which charged droplets and a buffer gas that transports neutral droplets or vapors enter through capillaries 4 and 16 and are piped together into the "pickup region" through a capillary 19. A fourth capillary 20 may be provided, through which only buffer gases containing vapors of interest can be transported into the "mixing chamber" 18. A fifth capillary 21 may also be added, through which the buffer gas can be exhausted to adjust the overall gas pressure to a value. The direction 13 of the ion motion in the mobility analyzer is inclined relative to the direction 14 of the beam of charged droplets by an inclination angle 15.

Similar to the first embodiment, the ion mobility analyzer 1 is depicted as an ion mobility spectrometer (IMS). Into the mobility analyzer 1, ions are accelerated through the grid 2; in the mobility analyzer 1, the ions are pulled by another electric field through a buffer gas and recorded in the ion detector 3.

From the appearance times of these ion signals, one can deduce the ion velocities in the mobility analyzer and thus the corresponding ion mobilities. As an alternative, one can also replace this detector 3 with an ion shutter that opens for a period, during which ions of a specific mobility may pass toward the entrance of a sequentially arranged mass spectrometer.

From the capillary 4 of an electrospray ion source charged droplets are piped into the mixing chamber 18 with the charged droplets being formed from a mixture of solvents which contain no more than a negligible amount of molecules of interest. Through the capillary 16 independently produced neutral droplets that have molecules of interest incorporated are piped into the mixing chamber 18 together with the buffer gas that may also contain some vapor of molecules of interest.

Via capillary 19, a portion of the mixture of the gas flows of capillaries 4 and 16 is carried into the "pickup region". Via capillary 20, additional gas can be introduced into the mixing chamber 18 controlling the buffer gas mixture, as well as its pressure, and via another capillary 21*a* portion of the buffer gas in the mixing chamber 18 is pumped off. From the capillary 19, the gas in the mixing chamber 18 that contains charged and neutral droplets emerges as a diverging beam 22 into the "pickup region". Either in the mixing chamber or in the pickup region; charged droplets can then fuse with neutral droplets, thus forming larger charged droplets, and free molecules can adsorb at charged initial droplets or at the new larger fused droplets.

The direction of the motion 13 of ions in the mobility analyzer is inclined to the direction 14 of the beam of charged droplets under the inclination angle 15, which may be chosen such that most of the molecule ions but substantially none of the neutral and charged droplets can enter the ion mobility spectrometer.

In the foregoing cases, the incorporated molecules of interest are ionized when the liquid of the charged droplets evaporates, and the droplet charge is transferred to the incorporated molecules.

According to the exemplary embodiments, the mobility analyzer 1 may be used as a mobility separator that passes, at different times, ions of different mobilities to a sequentially arranged second mobility layer, or a mass spectrometer. In parallel the mobility analyzer may operate as a mobility spectrometer, such that ions of different mobilities are recorded at different times, so that additionally a mobility spectrum (or series of mobility spectra) are obtained.

Additionally, respective gas pressures in the ion mobility analyzer and in the pickup region may be substantially equal or the gas pressure of the ion mobility analyzer may be at least 20 mbar higher or lower than the gas pressure of the pickup region. Further, the gas pressure in the mobility analyzer may be approximately that of ambient pressure, or substantially lower than the ambient pressure.

In the foregoing embodiments, the liquid in the charged droplets may evaporate in a heated desolvation region that is separate or integral with respect to the "pickup region".

Also, in the foregoing embodiments, the mobility analyzer may operate as a mobility filter that sends at least a portion of the mobility analyzed ions to another mobility analyzer for further mobility analysis, and/or to a mass spectrometer to record mass spectra of the mobility selected ions, wherein the mobilities (K) of the portion of mobility-analyzed ions are at least one of (a) below a maximum mobility (Kmax≧K), and (b) below the maximum mobility and above a minimum mobility (Kmax≧K≧min).

The foregoing embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ion mobility analyzer comprising at least one of (a) a "differential mobility analyzer" (DMA), (b) an "ion mobility spectrometer" (IMS) and (c) a "differential mobility spectrometer" (DMS), to which charged molecules of interest are fed, wherein ions are fed to the ion mobility analyzer from a "droplet pickup ion source" comprising an electrospray ion source that forms charged droplets from a solvent mixture in which substantially no amount of the molecules of interest are dissolved, and said charged droplets are pulled by an electric field into a "pickup region" which can be either the surface of a solid or liquid sample or a volume filled with a buffer gas at a pressure in which pickup region said charged droplets incorporate said molecules of interest and transfer the charge of said charged droplets to said molecules of interest, when the liquid in said charged droplets has evaporated in a heated desolvation region that is separate or integral with respect to said "pickup region".

2. The ion mobility analyzer of claim 1, wherein in said "pickup region" that is positioned between the electrospray ion source and the mobility analyzer, said molecules of interest exist as free molecules that are desorbed from a sample by a laser beam or a beam of energetic particles impacting onto said sample, wherein the sample is one of a solid and a liquid.

3. The ion mobility analyzer of claim 2, wherein said laser beam is focused to a point of a surface of said sample.

4. The ion mobility analyzer of claim 3, wherein said focused laser beam is scanned across the surface of said sample by at least one of (a) deflecting the laser beam and (b) moving the sample, so that a spot of the focus laser beam is moved across the sample.

5. The ion mobility analyzer of claim 4, wherein at least one of obtained mobility spectra and mobility selected mass spectra is used to determine a local distribution of different ones of the molecules of interest across the sample.

6. The ion mobility analyzer of claim 3, wherein the sample is at least a portion of an effluent of a liquid chromatograph, and mobility spectra change with time when new ones of the molecules of interest appear in said effluent of said liquid chromatograph.

7. The ion mobility analyzer of claim 1, wherein in said "pickup region", said molecules of interest exist as free molecules after being brought into said "pickup region" via a separate capillary as a vapor in a buffer gas.

8. The ion mobility analyzer of claim 7, wherein said vapor and said buffer gas comprise at least a portion of an effluent of a gas chromatograph, and mobility spectra change with time when new ones of said molecules of interest appear in said effluent of said gas chromatograph.

9. The ion mobility analyzer of claim 8 in which case the plume of the charged droplets is pushed at different times towards different positions of the sample so that said charged droplets effectively scan the surface of the sample and at least one of the mobility spectra or mobility selected mass spectra is used to determine a local distribution of different ones of the molecules of interest across the sample.

10. The ion mobility analyzer of claim 1 wherein said charged droplets interact with the surface of a solid or liquid sample directly in which process molecules of interest are incorporated into said charged droplets.

11. The ion mobility analyzer of claim 1, wherein a separate capillary is added, through which independently produced neutral droplets that contain said molecules of interest are brought into said "pickup region", either as molecules dissolved in the liquid of said neutral droplets or as molecules that were incorporated into said neutral droplets upstream from said "pickup region" when said neutral droplets interacted with a sample surface or when said neutral droplets passed through a buffer gas in which molecules of interest existed as molecules in a vapor or as molecules desorbed from a liquid or solid target by the impact of a laser beam or a beam of energetic particles.

12. The ion mobility analyzer of claim 11, wherein said neutral droplets either fuse in said "pickup region" with said charged droplets, or after the liquid of said neutral droplets in said "pickup region" evaporates and the molecules of interest exist as free molecules that can adsorb at the surfaces of said charged droplets, wherein said "pickup region"-charged droplets exist that have incorporated molecules of interest, and when the liquid of said charged droplets evaporates, the droplets transfer a charge of the droplet to the molecules of interest.

13. The ion mobility analyzer of claim 12, wherein incorporation of the molecules of interest into charged droplets occurs partially in a mixing chamber into which neutral droplets and charged droplets are brought via respective separate capillaries, and wherein the gas from said mixing chamber is conducted to said "pickup region" through another capillary, while through a further capillary, a buffer gas is brought into the mixing chamber, or through a further added capillary, a part of the gas in said mixing chamber is exhausted.

14. The ion mobility analyzer of claim 1, wherein the mobility analyzer operates as a mobility spectrometer, in which at least some of the ions of different mobilities are recorded at different times, so that one mobility spectrum or a series of mobility spectra is obtained.

15. The ion mobility analyzer of claim 14, wherein when ions of a specific mobility are recorded, a portion of the ions is allowed to move to another mobility analyzer for further mobility analysis, and/or to a mass spectrometer to record mass spectra of the mobility selected ions.

16. The ion mobility analyzer of claim 1, wherein the mobility analyzer operates as a mobility filter that sends at least a portion of the mobility analyzed ions to another mobility analyzer for further mobility analysis, and/or to a mass spectrometer to record mass spectra of the mobility selected ions, wherein the mobilities (K) of the portion of mobility-analyzed ions are at least one of (a) below a maximum mobility ($K_{max} \geq K$) and (b) below the maximum mobility and above a minimum mobility ($K_{max} \geq K \geq K_{min}$).

17. The ion mobility analyzer of claim 1, wherein the mobility analyzer is a time dependent mobility separator that passes, at different times, ions of different mobilities to a sequentially arranged second mobility analyzer or a mass spectrometer.

18. The ion mobility analyzer of claim 1, wherein respective gas pressures in said ion mobility analyzer and in said "pickup region" are substantially equal.

19. The ion mobility analyzer of claim 1, wherein a gas pressure of said ion mobility analyzer is at least 20 mbar higher or lower than a gas pressure of the "pickup region".

20. The ion mobility analyzer of claim 1, wherein the gas pressure in the mobility analyzer is approximately that of ambient pressure.

21. The ion mobility analyzer of claim 1, wherein the gas pressure in the mobility analyzer is substantially lower than ambient pressure.

* * * * *